United States Patent
Loo et al.

(10) Patent No.: US 11,317,531 B2
(45) Date of Patent: Apr. 26, 2022

(54) MICROELECTRONIC DEVICE AND CIRCUIT BOARD THEREOF

(71) Applicant: ALTEK BIOTECHNOLOGY CORPORATION, Hsinchu (TW)

(72) Inventors: Hsi-Hsin Loo, Hsinchu (TW); Chun-Wei Liu, Hsinchu (TW); Chao-Yu Chou, Hsinchu (TW)

(73) Assignee: ALTEK BIOTECHNOLOGY CORPORATION, Hsinchu (TW)

( * ) Notice: Subject to any disclaimer, the term of this patent is extended or adjusted under 35 U.S.C. 154(b) by 0 days.

(21) Appl. No.: 16/510,349

(22) Filed: Jul. 12, 2019

(65) Prior Publication Data

US 2020/0221598 A1    Jul. 9, 2020

(30) Foreign Application Priority Data

Jan. 9, 2019    (TW) ................. 108100878

(51) Int. Cl.
*H05K 1/11*    (2006.01)
*H05K 7/14*    (2006.01)
(Continued)

(52) U.S. Cl.
CPC ........... *H05K 7/1427* (2013.01); *H05K 1/115* (2013.01); *H05K 1/181* (2013.01); *A61B 1/0008* (2013.01);
(Continued)

(58) Field of Classification Search
CPC ...... H05K 7/1427; H05K 1/115; H05K 1/181; H05K 1/184; H05K 1/188; H05K 1/0207; H05K 3/4685
See application file for complete search history.

(56) References Cited

U.S. PATENT DOCUMENTS 5,365,268 A * 11/1994 Minami .................. A61B 1/05
257/E31.118
5,991,162 A * 11/1999 Saso .................... H05K 1/0207
257/700

(Continued)

FOREIGN PATENT DOCUMENTS

CN    201332093 Y    10/2009
CN    202750332 U    2/2013
(Continued)

*Primary Examiner* — Abhishek M Rathod
*Assistant Examiner* — Keith DePew
(74) *Attorney, Agent, or Firm* — Li & Cai Intellectual Property (USA) Office

(57) ABSTRACT

A microelectronic device includes an accommodating housing, a circuit board, an electronic component, and a conducting wire. The accommodating housing has an accommodating space therein. The circuit board is disposed within the accommodating space, and has a first and a second end surface disposed opposite to each other. The first end surface includes a first conductive contact, and a lateral side of the circuit board includes a receiving hole being a half-open hole extending from the second end surface. A second conductive contact is disposed on the surface of the receiving hole and electrically connected to the first conductive contact via an internal power layer of the circuit board. The electronic component is disposed on the first end surface and electrically connected to the first conductive contact. One end of the conducting wire is disposed in the receiving hole and electrically connected to the second conductive contact.

18 Claims, 6 Drawing Sheets

(51) Int. Cl.
*H05K 1/18* (2006.01)
*A61B 1/00* (2006.01)

(52) U.S. Cl.
CPC .............. *H05K 2201/09509* (2013.01); *H05K 2201/10151* (2013.01)

(56) References Cited

U.S. PATENT DOCUMENTS

| | | | | |
|---|---|---|---|---|
| 6,105,246 | A * | 8/2000 | Houser | H05K 3/0052 174/262 |
| 6,494,739 | B1 * | 12/2002 | Vivenzio | H01R 13/5804 358/473 |
| 6,547,721 | B1 * | 4/2003 | Higuma | A61B 1/051 600/133 |
| 6,717,820 | B1 * | 4/2004 | Loh | H01L 31/0203 257/E31.118 |
| 6,817,870 | B1 * | 11/2004 | Kwong | H01R 12/523 439/74 |
| 7,074,181 | B2 * | 7/2006 | Futatsugi | A61B 1/05 600/110 |
| 8,366,920 | B2 * | 2/2013 | Davis | B67D 3/0032 210/86 |
| 9,706,092 | B1 * | 7/2017 | Tam | H04N 5/2254 |
| 10,582,839 | B2 * | 3/2020 | Igarashi | H04N 5/2253 |
| 10,939,803 | B2 * | 3/2021 | Viebach | A61B 1/015 |
| 2002/0062084 | A1 * | 5/2002 | Ohara | A61B 8/4416 600/462 |
| 2003/0232460 | A1 * | 12/2003 | Poo | H01L 25/105 438/106 |
| 2004/0147807 | A1 * | 7/2004 | Viebach | A61B 1/00096 600/129 |
| 2004/0263680 | A1 * | 12/2004 | Sonnenschein | H04N 5/2253 348/375 |
| 2005/0225955 | A1 * | 10/2005 | Grebenkemper | H05K 1/0218 361/780 |
| 2006/0062418 | A1 * | 3/2006 | Hashiba | H04R 1/06 381/386 |
| 2006/0109368 | A1 * | 5/2006 | Ayrenschmalz | H01L 27/14636 348/340 |
| 2006/0237223 | A1 * | 10/2006 | Chen | H05K 1/0218 174/255 |
| 2009/0021618 | A1 * | 1/2009 | Schwarz | A61B 1/051 348/294 |
| 2011/0313252 | A1 * | 12/2011 | Lin | A61B 1/05 600/162 |
| 2012/0104230 | A1 * | 5/2012 | Eismann | H04N 5/2253 250/208.1 |
| 2012/0118622 | A1 * | 5/2012 | Gruendler | H05K 1/162 174/260 |
| 2012/0206583 | A1 * | 8/2012 | Hoshi | H04N 5/2253 348/76 |
| 2012/0247825 | A1 * | 10/2012 | Wei | H05K 1/0222 174/266 |
| 2014/0003018 | A1 * | 1/2014 | Fujimori | H05K 3/10 361/783 |
| 2016/0072989 | A1 * | 3/2016 | Kennedy, II | H04N 5/2253 348/76 |
| 2017/0086660 | A1 * | 3/2017 | Igarashi | H05K 3/361 |
| 2017/0118844 | A1 * | 4/2017 | Chamberlin | H05K 3/0047 |
| 2017/0127915 | A1 * | 5/2017 | Viebach | A61B 1/00011 |
| 2017/0127921 | A1 * | 5/2017 | Motohara | A61B 1/127 |
| 2018/0168041 | A1 * | 6/2018 | Govrin | A61B 1/051 |
| 2018/0325360 | A1 * | 11/2018 | Sekido | A61B 1/00114 |
| 2018/0325364 | A1 * | 11/2018 | Okamura | H01L 27/14636 |
| 2019/0021582 | A1 * | 1/2019 | Shimizu | H01L 27/14618 |
| 2019/0021696 | A1 * | 1/2019 | Morimoto | A61B 8/12 |
| 2019/0038257 | A1 * | 2/2019 | Yamamoto | B06B 1/0622 |
| 2019/0296537 | A1 * | 9/2019 | Mikami | H01R 43/28 |
| 2019/0335068 | A1 * | 10/2019 | Kato | A61B 1/00114 |
| 2020/0000328 | A1 * | 1/2020 | Sakai | A61B 1/00018 |

FOREIGN PATENT DOCUMENTS

| | | |
|---|---|---|
| CN | 106059617 A | 10/2016 |
| CN | 207236763 U | 4/2018 |
| CN | 108135083 A | 6/2018 |
| TW | 200412219 A | 7/2004 |
| TW | M564312 U | 7/2018 |
| WO | 2018021061 A1 | 2/2018 |

* cited by examiner

MICROELECTRONIC DEVICE AND CIRCUIT BOARD THEREOF

CROSS-REFERENCE TO RELATED PATENT APPLICATION

This application claims the benefit of priority to Taiwan Patent Application No. 108100878, filed on Jan. 9, 2019. The entire content of the above identified application is incorporated herein by reference.

Some references, which may include patents, patent applications and various publications, may be cited and discussed in the description of this disclosure. The citation and/or discussion of such references is provided merely to clarify the description of the present disclosure and is not an admission that any such reference is "prior art" to the disclosure described herein. All references cited and discussed in this specification are incorporated herein by reference in their entireties and to the same extent as if each reference was individually incorporated by reference.

FIELD OF THE DISCLOSURE

The present disclosure relates to a microelectronic device and circuit board thereof, and more particularly to a micro circuit board structure with a half-open hole.

BACKGROUND OF THE DISCLOSURE

With the development of microelectronic technique and technology, various microelectronic devices have been afforded a wider range of application. For example, in the military, medical, aerospace, and industrial fields, as well as in general consumer supplies, various multifunctional, sophisticated and miniaturized electronic devices have been developed.

In order to meet the requirements of the electronic devices with various different functions, different electronic components (e.g., processors, memories or sensors) with different functions are disposed on the circuit board, so that the electronic components can cooperate and work with each other. In order to supply power for the electronic components or to transmit electrical signals transmitted and received by the electronic components, aside from the original circuit layout, conducting wires also need to be additionally welded on the circuit board. However, as devices are increasingly being miniaturized, it is difficult to successfully connect the conducting wire to the circuit board of the microelectronic device in a stable manner.

Taking an endoscope device as an example, the endoscope is usually used for medical purposes to assist medical personnel in observing the internal environment of a human body, which cannot be observed with the naked eye, for example, conditions in the gastrointestinal tract, respiratory tract or female reproductive system, and also examination of interior cavities such as the abdominal cavity, joint cavity, chest cavity or amniotic cavity after a minimally invasive surgery. In addition, the endoscope is often used in the fields of construction or electronic instrument detection to perform inspection operations in narrow gaps.

Generally, the endoscope must have a lens or sensors disposed on the circuit board to capture image information. The aforementioned lens or sensors and the circuit board are often installed together within an accommodating housing (e.g., lens holder) to fix the lens and the circuit board in the position, and then the accommodating case and the lens therein and the circuit board are installed together within a tube. In order to achieve the purpose of deep penetration, the diameter of the pipeline of the endoscope should be as small as possible. In particular, when the endoscope is applied for the medical purposes, the miniaturized endoscope is useful for reducing the suffering of the patient. However, in order to obtain images with a better quality, it is necessary to use a lens or sensors with better resolution, but such lens or sensors usually have larger sizes.

Obviously, as the device becomes smaller and smaller, the internal space of the endoscope is increasingly limited. Moreover, not only will the lens and the sensors occupy a large space, but the light emitting component or the fiber cable is required to be disposed on the circuit board to introduce external light. Furthermore, the endoscope for medical use must be sleeved within the tube to allow the working channel to be installed, so that scissors, clips, hemostats and so on can pass through the working channel. Apparently, in the microelectronic device, the internal components and the conducting wire are difficult to be arranged.

In the related art, one of the solutions is to weld the conducting wire vertically on the circuit board within limited space such that the conducting wire is able to be electrically connected to the conducting wire on the circuit board. However, with the aforementioned solution, not only is the welding process difficult, but the resulting strength of the structure would be poor. During the operation of the endoscope, the conducting wire could easily detach from the welding. Another solution of the related art is to bend one end of the conducting wire and then lay the bent portion on the surface of the circuit board for welding so as to obtain a better stability of the structure. However, according to the aforementioned description, as the device becomes smaller, it is also difficult to reserve enough welding area and wiring space, thus rendering the aforementioned solution less than ideal.

Accordingly, how the stability of the connection between the conducting wire and the circuit board can be enhanced by the improvement of the structure design, under the condition that the electronic components are required to be disposed within limit space, has become one of the most important topics in the related art.

SUMMARY OF THE DISCLOSURE

The present disclosure provides a microelectronic device and a circuit board thereof that can address the drawbacks of the related art. Therefore, a stable connection between the conducting wire and the circuit board within limited space is provided to enhance the production yield and durability of the microelectronic device.

In response to the above-referenced technical inadequacies, the present disclosure provides a microelectronic device includes an accommodating housing, a circuit board, at least one electronic component and at least one conducting wire. The accommodating housing has an accommodating space therein. The circuit board is disposed within the accommodating space and includes a first end surface, a second end surface and at least one receiving hole. The first end surface includes at least one first conductive contact, and the second end surface is opposite to the first end surface. The at least one receiving hole is located on a lateral side of the circuit board and is a half-open hole extending from the second end surface, and a surface of the at least one receiving hole includes a second conductive contact. The second conductive contact passes through at least one internal power layer of the circuit board to be electrically connected to the first conductive contact. The at least one electronic component is disposed on the first end surface and electrically connected to the at least one conductive contact. One end of the at least one conducting wire is disposed within the at least one receiving hole, and the at least one conducting wire is electrically connected to the second conductive contact.

In certain embodiments, the at least one receiving hole is a blind hole extending from the second end surface.

In certain embodiments, a range of a depth of the at least one receiving hole is ½ to ⅘ of a thickness of the circuit board.

In certain embodiments, an inner layer of the circuit board includes at least two fixing flanges, and the at least two fixing flanges are integrated with the second conductive contact.

In certain embodiments, a distribution range of the fixing flange is ⅙ to ½ of a depth of the at least one receiving hole.

In response to the above-referenced technical inadequacies, the present disclosure also provides a circuit board, and the circuit board includes a first end surface, a second end surface, at least one receiving hole and at least one internal power layer. The first end surface includes at least one first conductive contact. The second end surface is opposite to the first end surface. The at least one receiving hole is located on a lateral side of the circuit board and is a half-open hole extending from the second end surface, and a surface of the at least one receiving hole includes a second conductive contact. The second conductive contact passes through at least one internal power layer of the circuit board to be electrically connected to the first conductive contact. The at least one internal power layer is electrically connected to the first conductive contact and the second conductive contact.

Therefore, one of the advantages in the present disclosure is to provide a stable connection between the conducting wire and the circuit board within a limited space by the at least one first conductive contact disposed on the first end surface, the receiving hole disposed at the lateral side of the circuit board, the receiving hole is a half-open hole extending from the second end surface, the second conductive contact disposed on the surface of the receiving hole, and the second conductive contact electrically connected to the first conductive contact via the internal power layer. The conducting wire is used to provide electric power for the electronic component or transmit the electric signal transmitted and received by the electronic component.

These and other aspects of the present disclosure will become apparent from the following description of the embodiment taken in conjunction with the following drawings and their captions, although variations and modifications therein may be affected without departing from the spirit and scope of the novel concepts of the disclosure.

BRIEF DESCRIPTION OF THE DRAWINGS

The present disclosure will become more fully understood from the detailed description and the accompanying drawings, in which.

DETAILED DESCRIPTION OF THE EXEMPLARY EMBODIMENTS

Figure 1:
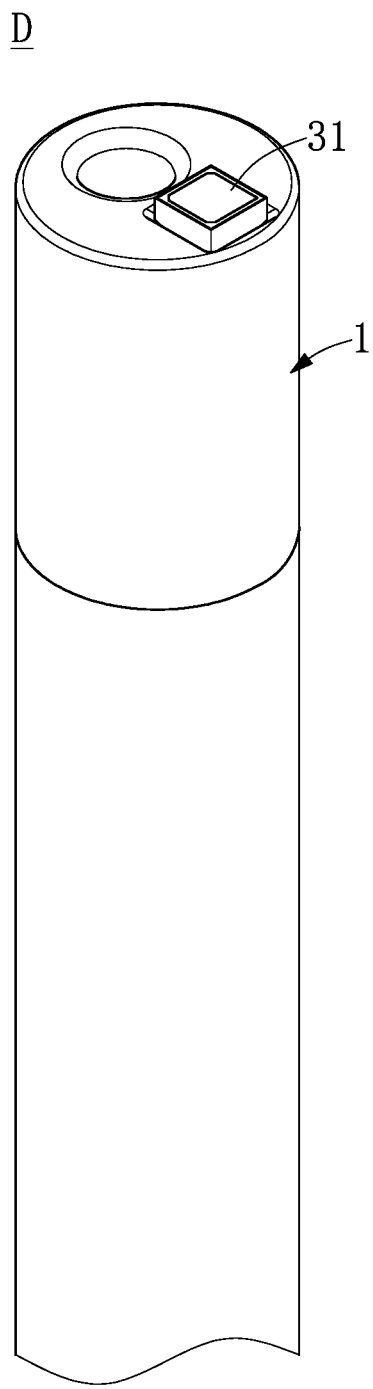
FIG. 1 is a perspective schematic view of a microelectronic device in one embodiment of the present disclosure.

The present disclosure is more particularly described in the following examples that are intended as illustrative only since numerous modifications and variations therein will be apparent to those skilled in the art. Like numbers in the drawings indicate like components throughout the views. As used in the description herein and throughout the claims that follow, unless the context clearly dictates otherwise, the meaning of "a", "an", and "the" includes plural reference, and the meaning of "in" includes "in" and "on". Titles or subtitles can be used herein for the convenience of a reader, which shall have no influence on the scope of the present disclosure.

The terms used herein generally have their ordinary meanings in the art. In the case of conflict, the present document, including any definitions given herein, will prevail. The same thing can be expressed in more than one way. Alternative language and synonyms can be used for any term(s) discussed herein, and no special significance is to be placed upon whether a term is elaborated or discussed herein. A recital of one or more synonyms does not exclude the use of other synonyms. The use of examples anywhere in this specification including examples of any terms is illustrative only, and in no way limits the scope and meaning of the present disclosure or of any exemplified term. Likewise, the present disclosure is not limited to various embodiments given herein. Numbering terms such as "first", "second" or "third" can be used to describe various components, signals or the like, which are for distinguishing one component/signal from another one only, and are not intended to, nor should be construed to impose any substantive limitations on the components, signals or the like.

Figure 2:
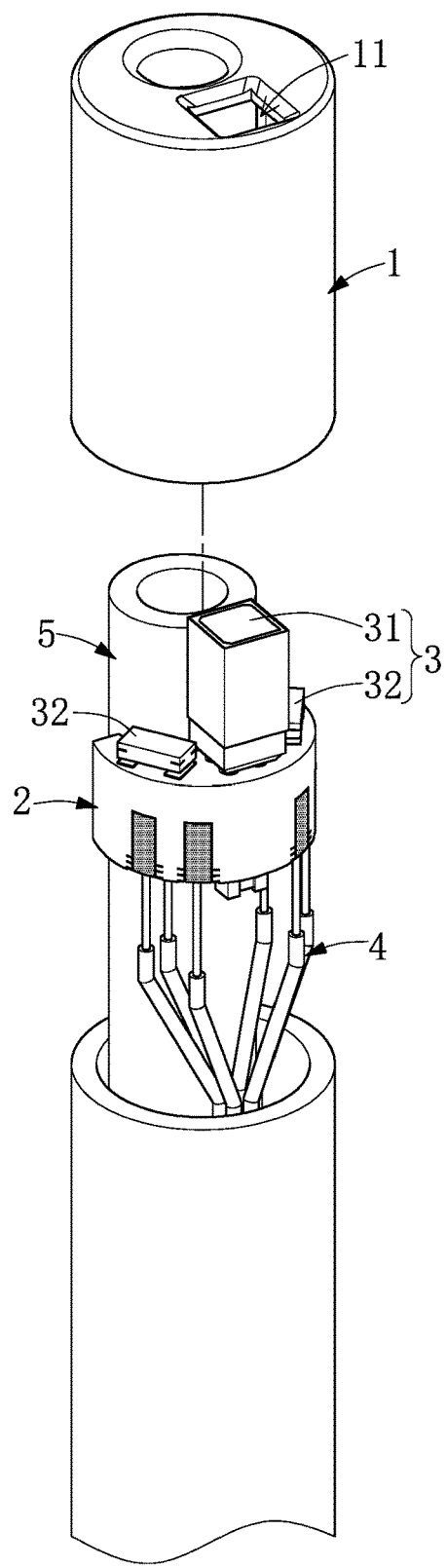
FIG. 2 is another perspective schematic view of the microelectronic device in the embodiment of the present disclosure.

With reference to FIG. 1 and FIG. 2, FIG. 1 is a perspective schematic view of a microelectronic device in an embodiment of the present disclosure and FIG. 2 is another perspective schematic view of the microelectronic device in the embodiment of the present disclosure. A microelectronic device is provided in the embodiment of the present disclosure. In the present embodiment, the microelectronic device D is exemplified as an endoscope, but it is not limited thereto. In other devices aiming toward miniaturization, when the arrangement of components is limited by space and there is difficulty in wire connection, the arrangement provided in the present disclosure can also be implemented in their product design. In the present embodiment, the microelectronic device D includes an accommodating housing 1, a circuit board 2, at least one electronic component 3, at least one conducting wire 4, and a working channel 5. Further illustration of the structure of the aforementioned components will be described in the following.

Figure 3:
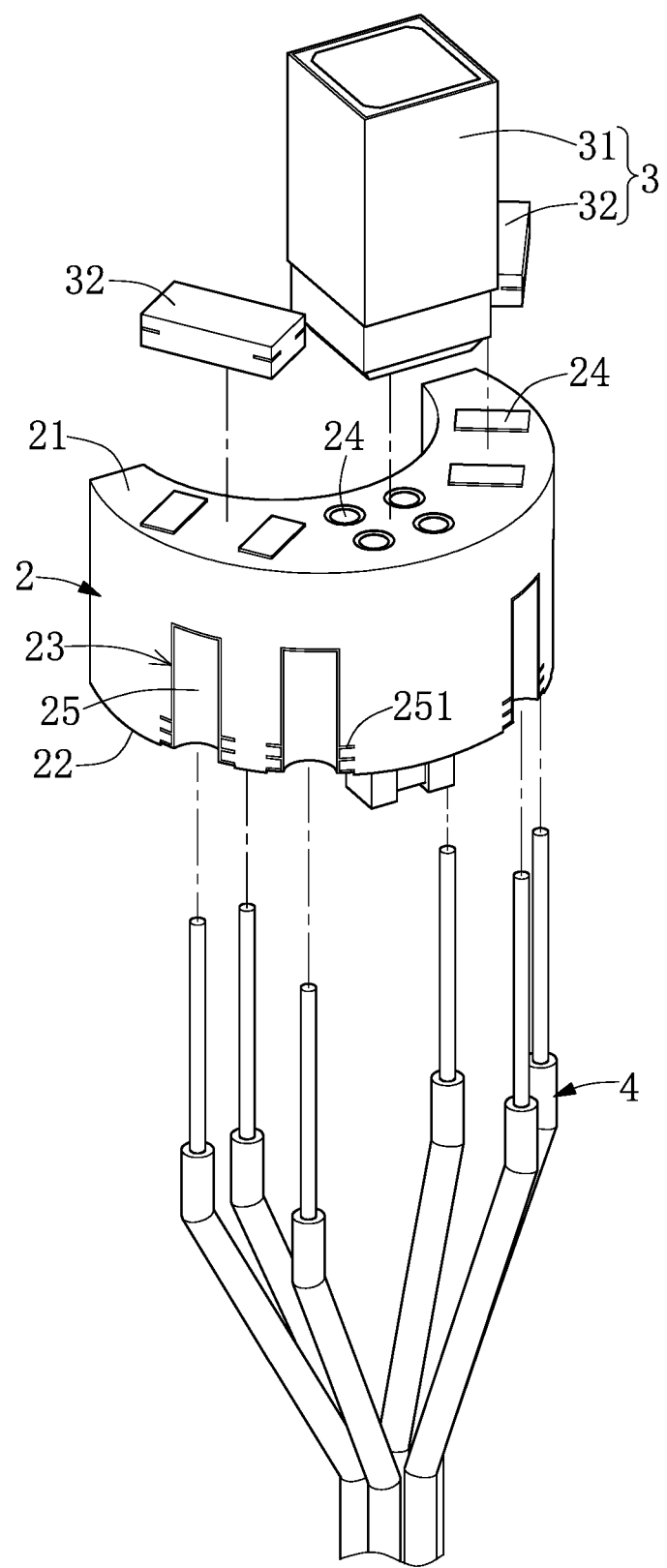
FIG. 3 is a perspective exploded view of the microelectronic device in the embodiment of the present disclosure.
Figure 4:
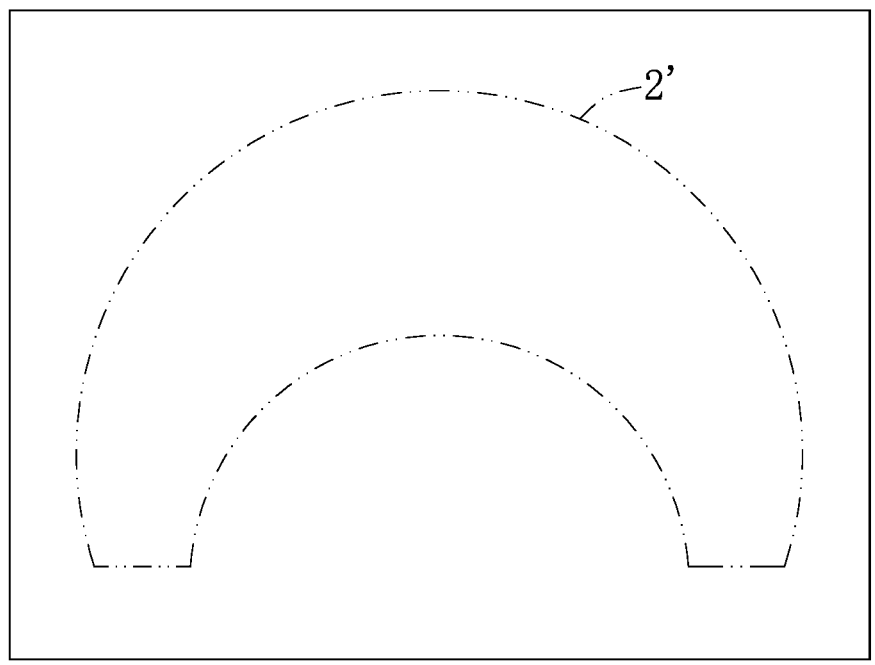
FIG. 4 is a bottom view of a multi-layer board without holes in the embodiment of the present disclosure.

Then, with reference to FIG. 2 and FIG. 3, FIG. 3 is a perspective exploded view of the microelectronic device in the embodiment of the present disclosure. In the embodiment of the present disclosure, the accommodating housing 1 has an accommodating space 11 therein, and the circuit board 2, the electronic component 3 and the conducting wire 4 are disposed within the accommodating space 11. In the present embodiment, the accommodating housing 1 can be a lens holder for fixing a lens and the circuit board 2 in place, or can be a tube body sleeved around the endoscope. The circuit board 2 includes a first end surface 21 and a second end surface 22, and the first end surface 21 is opposite to the second end surface 22. The first end surface 21 can be a component layer and is also called a top layer of the circuit board 2, and the second end surface 22 can be a welding layer and is also called a bottom layer of the circuit board 2. In the embodiment of the present disclosure, the first end surface 21 includes at least one conductive contact 24, and the conductive contact 24 can be a metal wire disposed on the first end surface 21 or a connecting point or pad disposed within the circuit board 2 and exposed on the first end surface 21. Any contacting points for electrically connection on the first end surface 21 can be the first conductive contact 24 in the present disclosure. Accordingly, the electronic component 3 can be disposed on the first conductive contact 24 of the circuit board 2, so that the electronic component 3 is electrically connected to the first conductive contact 24. In the present embodiment, the electronic component 3 disposed on the first end surface 21 of the circuit board 2 includes an image sensor 31 and a light emitting component 32. However, in practical applications, as the endoscope is made in accordance with the design of the present disclosure, a fiber cable is installed and passes through the first end surface 21 and the second end surface 22. The light is transmitted by the fiber cable, so that only an image sensor 31 of the electronic component 3 is disposed on the first end surface 21.

Accordingly, the at least one receiving hole 23 is disposed on a lateral side of the circuit board 2. The receiving hole 23 is a half-open hole extending from the second end surface 22. Specifically, in the present embodiment, the receiving hole 23 is a blind hole extending from the second end surface 22 but not passing through the first end surface 21. Since the receiving hole 23 does not pass through the first end surface 21, the area of the first end surface 21 will not be reduced and there are more spaces on the first end surface 21 for disposing any different kinds of the electronic components 3. The surface of the receiving hole 23 includes a second conductive contact 24. One end of the conducting wire 4 is disposed within the receiving hole 23 and is electrically connected to the second conductive contact 25. In addition, one end of the conducting wire 4 is fixed within the receiving hole 23 by welding materials.

Figure 5:
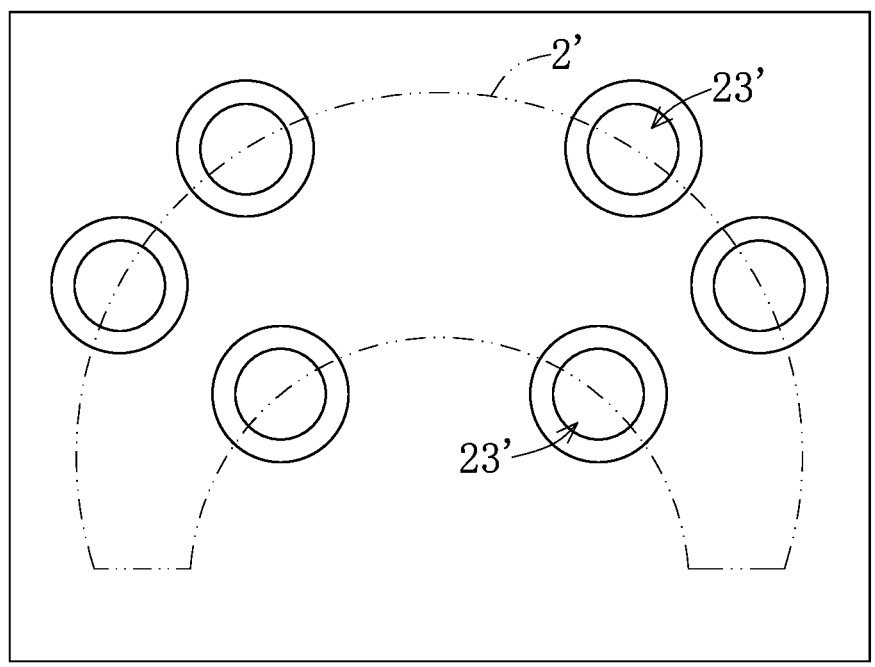
FIG. 5 is a bottom view of the multi-layer board having a plurality of blind holes drilled thereon in the embodiment of the present disclosure.
Figure 6:
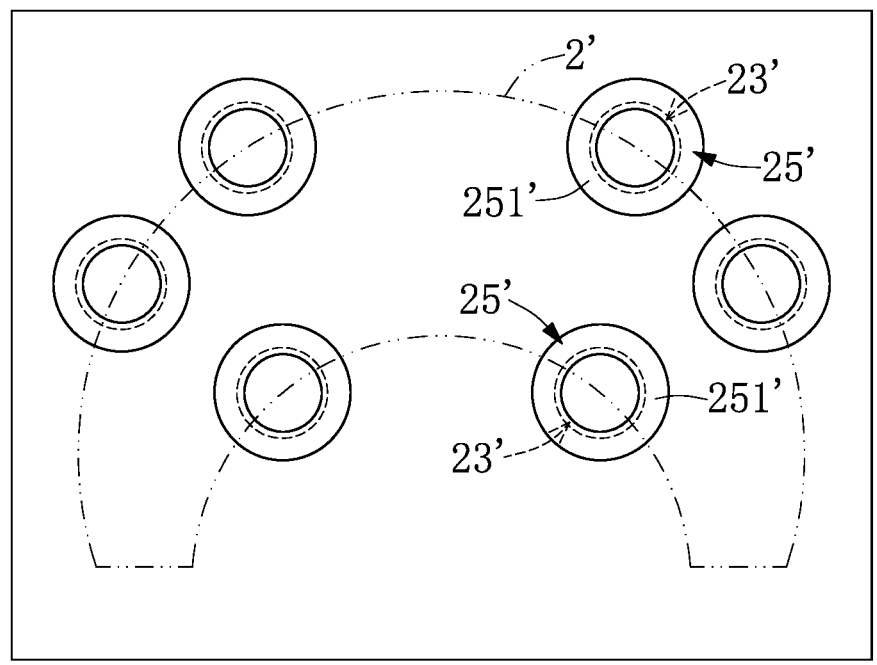
FIG. 6 is a bottom view of the blind hole welded with a metal layer in the embodiment of the present disclosure.
Figure 7:
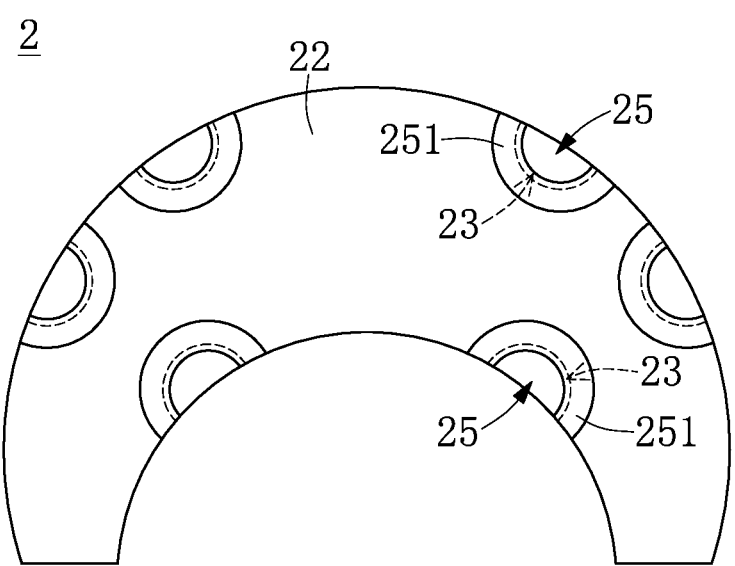
FIG. 7 is a bottom of the circuit board having a milling formation in the embodiment of the present disclosure.
Figure 8:
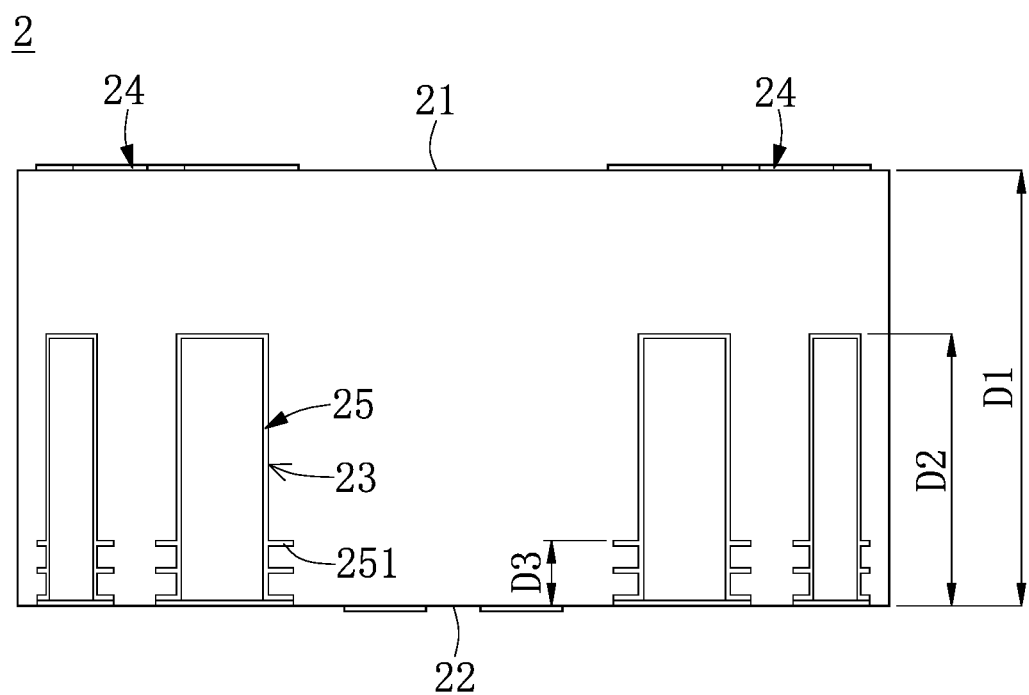
FIG. 8 is a side schematic view of the circuit board in the embodiment of the present disclosure.

With reference to FIG. 3 and FIG. 4-FIG. 7, FIG. 4 is a bottom view of a multi-layer board without holes in the embodiment of the present disclosure; FIG. 5 is a bottom view of the multi-layer board having a plurality of blind holes drilled thereon in the embodiment of the present disclosure; FIG. 6 is a bottom view of the blind hole welded with a metal layer in the embodiment of the present disclosure; and FIG. 7 is a bottom view of the circuit board having a milling formation in the embodiment of the present disclosure. In the embodiment of the present disclosure, the second conductive contact 25 is a metal welding layer coated on the internal surface of the receiving hole 23 by an electroplating technique, so that the conducting wire 4 can be electrically connected to the second conductive contact 25. In the actual manufacturing process, a plurality of blind holes 23' is drilled on the multi-layer board 2' that is larger, and the electroplating solution is filled within the blind holes 23' to perform electroplating, so that the metal layer 25' is covered and formed on the internal surface of the blind hole 23'. After all of the internal surfaces of the blind holes 23' are coated by the metal layer 25', the multi-layer board 2' is cut in a milling manner to form the final appearance of the multi-layer board 2'. In addition, the receiving holes 23 are formed on the lateral side of the circuit board 2, so that the metal layer 25' welded on the surface of the blind holes 23' is used as the second conductive contact 25. The second conductive contact 25 is electrically connected to the first conductive contact 24 via at least one internal power layer of the circuit board 2 so as to achieve the conduction of the circuit. According to practical requirement, a plurality of middle layers can be installed within the circuit board 2 for connection.

It should be noted that the receiving holes 23 is described as the half-open hole in the present disclosure, but the cross-section of the receiving hole 23 does not need to exactly or approximately form a half circle. According to practical requirement in spatial arrangement, the receiving hole 23, which is formed after cutting, can be ¼ (e.g., the central angle is 90°) to ⅓ (e.g., the central angle is 120°) of the area of the original blind hole 23'. The receiving hole 23 formed on the lateral side of the circuit board 2 is a recess structure capable of accommodating the conducting wire 4. More specifically, in the embodiment, the depth D2 of the recession of the receiving hole 23 from the lateral side of the circuit board 2 is between 0.2 and 0.8 mm, so that the conducting wire 4 can be installed within the receiving hole 23. Moreover, in order to obtain a better conductive efficiency between the conducting wire 4 and the second conducting contact 25, in the embodiment, the length of the second conductive contact 25 along the recession curve is between 0.2 and 1.5 mm. The aforementioned reference value is adjusted in accordance with the wire diameter of the conducting wire 4, but the reference value can be increased or decreased as appropriate in accordance with the requirement of the structure design.

In addition, although the receiving hole 23 is the blind hole extending from the second end surface 22 and not passing through the first end surface 21 in the embodiment of the present disclosure, the receiving hole 23 can also be designed as a through hole passing through the first end surface 21 and the second end surface 22 in a different embodiment of the present disclosure. Alternatively, the receiving hole 23 can be designed as a cone-shaped hole, so that the opening at the second end surface 22 is greater than the opening at the first end surface 21. Moreover, the processing manner introduced in the present embodiment is to first form the entire blind hole 23', and then to form the receiving hole 23 by milling the circuit board 2, but the manner of forming the receiving hole 23 at the lateral side of the circuit board 2 can be different, and is not limited thereto.

Then, the detail of the receiving hole 23 will be described in the following. With reference to FIG. 4 to FIG. 8, FIG. 8 is a side schematic view of the circuit board 2 in the embodiment of the present disclosure. In the embodiment of the present disclosure, the thickness D1 of the circuit board 2 is between 1 mm and 3 mm, and the depth D2 of the receiving hole 23 is between 0.8 mm and 2 mm. The range of the depth D2 of the receiving hole 23 is ½ to ⅕ of a thickness D1 of the circuit board 2. For example, in the present embodiment, the thickness D1 of the circuit board 2 is 1.6 mm, the depth D2 of the receiving hole 23 is 1 mm, and the depth D2 of the receiving hole 23 is ⅝ of the thickness D1 of the circuit board 2. However, during the manufacturing process, the thickness D1 of the circuit board 2 and the depth D2 of the receiving hole 23 can be adjusted in accordance with practical requirements.

In addition, as aforementioned description, in the embodiment of the present disclosure, the blind hole 23' is first drilled on the multi-layer board 2', and then the receiving hole 23 with the half opening is formed in the milling manner after an electroplating process. Accordingly, if the adhesion between the metal layer 25' that is electroplated within the blind hole 23' and the circuit board 2 is not strong enough, the metal layer 25' is likely to peel off during the milling process. In order to avoid the occurrence of the aforementioned problem, in the embodiment, at least two internal metal layers 251' are installed within the circuit board 2. When the metal layer 25' is formed by the electroplating process, the internal metal layer 251' within the circuit board 2 may be integrated with the metal layer 25'. Specifically, since the circuit board 2 used in the present disclosure is the multi-layer board 2', the at least two internal metal layers 251' may be installed in advance at the position where the blind hole is drilled 23'. Therefore, after the blind hole 23' is drilled in the internal metal layers 251', the lateral side of the internal metal layers 251' will be exposed on the internal surface of the blind hole 23'. Then, once the metal layer 25' is formed and covered on the internal surface of the blind hole 23' in the electroplating manner, the internal metal layers 251' within the multi-layer board 2' and the metal layer 25' within the internal surface of the blind hole 23' are integrated to each other. During the process of milling the leftover board materials, the internal metal layer 251' within the multi-layer board 2' can prevent the metal layer 25' covered on the internal surface of the blind hole 23' from peeling off by serving to anchor the metal layer 25' in place. Accordingly, after the process is completed, a plurality of fixing flanges 251 made by the internal metal layers 251' can be seen from the lateral side of the circuit board 2. In order to enhance the fixing effect, in the embodiment of the present disclosure, the fixing flanges 251 are disposed at different vertical positions in the receiving hole 23 to enhance the fixing effect on the second conductive contact 25. In the present embodiment, the fixing flanges 251 are close to the opening at one end of the second end surface 22 of the receiving hole 23. In practice, the distribution range D3 is ⅙ to ½ of the depth D2 of the receiving hole 23. More specifically, as aforementioned description, in the embodiment, the depth D2 of the receiving hole 23 is 1 mm, and the distribution range D3 of the fixing flanges 251 is about 0.3 mm. It should be noted that the internal metal layers 251' for forming the fixing flanges 251 may be isolated metal layers that are simply for enhancing the bonding force of the second conductive contact 25, and is only disposed at the periphery of the drilled position without connecting to other circuits. Alternatively, the middle layers within the circuit board 2 can be used as at least one of the internal metal layers 251' to concurrently provide fixing and signal transmission effects.

One of the advantages in the present disclosure is to provide a stable connection between the conducting wire 4 and the circuit board 2 within a limited space by the at least one first conductive contact 24 disposed on the first end surface 21, the receiving hole 23 disposed at the lateral side of the circuit board 2, the receiving hole 23 being the half-open hole extending from the second end surface 22, the second conductive contact 25 disposed on the surface of the receiving hole 23, and the second conductive contact 25 electrically connected to the first conductive contact 24 via the internal power layer. The conducting wire 4 is used to provide electric power for the electronic component 3 or transmit the electric signal transmitted and received by the electronic component 3.

Furthermore, the present disclosure provides the technical solution of the receiving end 23, which is a blind hole extending from the second end surface 22, so that there are more spaces reserved on the first end surface 21 for disposing any different kinds of the electronic components 3 so as to achieve the flexibility of the space usage.

Moreover, the present disclosure also provides the technical solution that the depth D2 of the receiving end 23 is between ½ and ⅘ of the thickness D1 of the circuit board 2 with consideration to the requirement of the wire arrangement and the overall structural strength of the circuit board 2.

In addition, the present disclosure further provides the technical solution that the at least two fixing flange 251 is disposed within the inner layer of the circuit board 2, the fixing flange is integrated with the second conductive contact and the distribution range D3 of the fixing flange 251 occupies ⅙ to ½ of the depth D2 of the receiving hole 23, so that the fixing flange 251 can be used to fasten the second conductive contact 25, which is covered on the internal surface of the receiving hole 23 to avoid the second conductive contact 25 being peeled off during the milling process when the fixing flange is formed on the half-open hole at the lateral side of the circuit board 2.

The foregoing description of the exemplary embodiments of the disclosure has been presented only for the purposes of illustration and description and is not intended to be exhaustive or to limit the disclosure to the precise forms disclosed. Many modifications and variations are possible in light of the above teaching.

The embodiments were chosen and described in order to explain the principles of the disclosure and their practical application so as to enable others skilled in the art to utilize the disclosure and various embodiments and with various modifications as are suited to the particular use contemplated. Alternative embodiments will become apparent to those skilled in the art to which the present disclosure pertains without departing from its spirit and scope.

What is claimed is:

1. An imaging device mounted on an endoscope with a working channel, the imaging device comprising:
   an image sensor configured to observe an internal environment of a target; and
   a circuit board electrically connected to the image sensor and a plurality of conducting wires, the circuit board including:
   a top end including a plurality of first conductive contacts electrically connected the image sensor;
   a bottom end;
   a lateral side surface formed and connected between the top end and the bottom end, and a shape of one portion of the lateral side surface matching an outer surface of the working channel; and
   a plurality of receiving holes formed correspondingly on one portion of the bottom end and one portion of the lateral side surface, and the plurality of receiving holes including a plurality of second conductive contacts respectively and electrically connected to the plurality of conducting wires;
   wherein each of the plurality of second conductive contacts includes a plurality of fixing flanges exposed from the lateral side surface and extending outward from the receiving hole along a direction parallel to the bottom end.

2. The imaging device according to claim 1, wherein a shape of the bottom end and a shape of the top end are similar.

3. The imaging device according to claim 1, further comprising:
at least one light emitting component;
wherein the at least one light emitting component and the image sensor are correspondingly and electrically connected to the plurality of first conductive contacts of the circuit board.

4. The imaging device according to claim 3, wherein the top end has a symmetrical shape with respect to an axis of symmetry, and the image sensor is disposed on the axis of symmetry.

5. The imaging device according to claim 4, wherein a number of the at least one light emitting component is even, and the even number of light emitting components are symmetrically disposed on the top end with respect to the axis of symmetry.

6. The imaging device according to claim 1, wherein the plurality of second conductive contacts are coating films.

7. The imaging device according to claim 1, wherein, along a thickness direction of the circuit board, a depth of the receiving hole is ½ to ⅘ of a thickness of the circuit board.

8. The imaging device according to claim 1, wherein the plurality of fixing flanges are one part of an internal metal layer of the circuit board.

9. The imaging device according to claim 1, wherein, along the thickness direction of the circuit board, a distribution range of the plurality of fixing flanges is ⅙ to ½ of a depth of the receiving hole.

10. An endoscope, comprising:
an accommodating housing;
a working channel disposed in the accommodating housing;
a plurality of conducting wires disposed in the accommodating housing; and
an image device disposed in the accommodating housing and against the working channel, and the image device including:
an image sensor configured to observe the internal environment of a target; and
a circuit board electrically connected to the image sensor and the plurality of conducting wires, and the circuit board including:
a top end including first conductive contacts electrically connected to the image sensor;
a bottom end;
a lateral side surface formed and connected between the top end and the bottom end, and a shape of one portion of the lateral side surface matching an outer surface of the working channel; and
a plurality of receiving holes formed correspondingly on one portion of the bottom end and one portion of the lateral side surface, and the plurality of receiving holes including a plurality of second conductive contacts respectively and electrically connected to the plurality of conducting wires;
wherein each of the plurality of second conductive contacts includes a plurality of fixing flanges exposed from the lateral side surface and extending outward from the receiving hole along a direction parallel to the bottom end.

11. The endoscope according to claim 10, wherein a shape of the bottom end and a shape of the top end are similar.

12. The endoscope according to claim 10, further comprising:
at least one light emitting component;
wherein the at least one light emitting component and the image sensor are correspondingly and electrically connected to the plurality of first conductive contacts of the circuit board.

13. The endoscope according to claim 12, wherein the top end has a symmetrical shape with respect to an axis of symmetry, and the image sensor is disposed on the axis of symmetry.

14. The endoscope according to claim 13, wherein a number of the at least one light emitting component is even, and the even number of light emitting components are symmetrically disposed on the top end with respect to the axis of symmetry.

15. The endoscope according to claim 10, wherein the plurality of second conductive contacts are coating films.

16. The endoscope according to claim 10, wherein, along a thickness direction of the circuit board, a depth of the receiving hole is ½ to ⅘ of a thickness of the circuit board.

17. The endoscope according to claim 10, wherein the plurality of fixing flanges are one part of an internal metal layer of the circuit board.

18. The endoscope according to claim 10, wherein, along the thickness direction of the circuit board, a distribution range of the plurality of fixing flanges is ⅙ to ½ of a depth of the receiving hole.

* * * * *